United States Patent [19]
Vlasblom

[11] Patent Number: 6,015,763
[45] Date of Patent: Jan. 18, 2000

[54] CLEANER IMPREGNATED TOWEL

[75] Inventor: Jack T. Vlasblom, Dunedin, Fla.

[73] Assignee: Dotolo Research Corp., Pinellas Park, Fla.

[21] Appl. No.: 09/024,430

[22] Filed: Feb. 17, 1998

[51] Int. Cl.⁷ .................................................. A01N 25/34

[52] U.S. Cl. ...................... 442/123; 428/305.5; 428/905; 424/404

[58] Field of Search ..................... 442/123, 59; 424/404; 428/305.5, 905

[56] References Cited

U.S. PATENT DOCUMENTS

| | | | |
|---|---|---|---|
| 5,540,853 | 7/1996 | Trinh et al. | 510/101 |
| 5,698,475 | 12/1997 | Vlasblom | 442/59 |

*Primary Examiner*—Elizabeth M. Cole
*Attorney, Agent, or Firm*—Donald R. Fraser

[57] ABSTRACT

A cleaner impregnated towel comprises a flexible, porous substrate and, impregnated into the substrate, a cleaner formulation comprising d-limonene, dibasic acid ester, N-methyl-2-pyrrolidone, secondary alcohol ethoxylate, sodium lauryl sulfate, polysorbate 80, glycerine, ethyl alcohol, an antimicrobial preservative, and optionally water.

26 Claims, No Drawings

CLEANER IMPREGNATED TOWEL

FIELD OF THE INVENTION

This invention relates generally to a cleaner impregnated towel. More particularly, the invention is directed to a non-woven or woven substrate that is impregnated with a cleaner, useful for cleansing the skin of a human being.

BACKGROUND OF THE INVENTION

Cleaners for cleansing the skin of humans are known in the art. Likewise, it is known to combine premeasured amounts of cleaners with articles such as pouches or flexible carrier sheets.

U.S. Pat. No. 4,938,888 to Kiefer et al. discloses a detergent sheet, comprising an alkyl polyglycoside and a detergency builder impregnated into a flexible substrate. The detergent formulation disclosed in Kiefer et al., however, is harsh and unsuitable for prolonged contact with human skin. Generally, the detergent sheets disclosed in the prior art contain detergents or other ingredients which irritate the skin.

A particularly useful and cost-effective cleaner impregnated towel is described in U.S. Pat. No. 5,698,475 to Vlasblom.

It would be desirable to develop an improved cleaner impregnated towel which is mild in contact with human skin, and which delivers copious quantities of stable foam.

SUMMARY OF THE INVENTION

Accordant with the present invention, an improved cleaner impregnated towel having the desirable qualities set forth above surprisingly has been discovered. The inventive cleaner impregnated towel comprises:

a flexible, porous substrate; and a cleaner impregnated into said substrate, said cleaner comprising:

from about 0.5 to about 90 weight percent d-limonene;

from about 0.5 to about 90 weight percent dibasic acid ester;

from about 0.5 to about 45 weight percent N-methyl-2-pyrrolidone;

from about 0.1 to about 50 weight percent secondary alcohol ethoxylate;

from about 0.1 to about 50 weight percent sodium lauryl sulfate;

from about 0.1 to about 50 weight percent polysorbate 80;

from about 0.1 to about 25 weight percent glycerine;

from about 0.1 to about 25 weight percent ethyl alcohol;

from about 0.01 to about 1 weight percent antimicrobial preservative; and optionally from 0 to about 95 weight percent water.

The cleaner impregnated towel according to the present invention is particularly useful for cleansing the skin of humans.

DETAILED BRIEF DESCRIPTION OF THE PREFERRED EMBODIMENT

The present invention is directed to a cleaner impregnated towel. The towel may be any conventional flexible, porous substrate, and the cleaner comprises d-limonene, dibasic acid ester, N-methyl-2-pyrrolidone, secondary alcohol ethoxylate, sodium lauryl sulfate, polysorbate 80, glycerine, ethyl alcohol, an antimicrobial preservative, and optionally water.

The flexible, porous substrate may comprise any monolithic flexible, porous material including, but not necessarily limited to, a non-woven or woven textile cloth or mat, a sponge material, paper, or the like. A preferred non-woven substrate would generally comprise adhesively bonded fibrous or filamentous materials having a web or carded fiber structure, or a mat in which the fibers are distributed either in a random fashion or in a substantially aligned manner. The fibers or filaments generally comprise natural materials, e.g., fibers or filaments of wood, silk, jute, hemp, cotton, linen, and the like, or synthetic materials, e.g., polyolefins, polyesters, rayon, cellulose esters, polyvinyl derivatives, polyamides, and the like, as well as combinations thereof.

The thickness of the substrate may vary over wide limits, and is generally of a thickness that will conveniently retain within its porous structure a quantity of an impregnated cleaner suitable for cleaning the skin of humans. Typically, the fibers or filaments have a Denier from about 1.5 to about 5, and are from about 5 mm to about 50 mm in length. Preferably, the fibers are at least partially randomly placed in the substrate and are adhesively bonded together with a substantially hydrophobic binder. A preferred flexible, porous substrate is available from The Dexter Corporation, Windsor Locks, Conn. under the product designation "HYDRASPUN."

The present invention also contemplates the impregnation of the non-aqueous formulation of the cleaner within the substrate. This effectively reduces the shipping weight of the product by substantially reducing the "bulk" therefrom. Thus, this alternative embodiment of the present invention provides a commercial advantage over most prior art detergent sheets which incorporate a liquid soap in pre-treated towels. The reduced shipping weight of the cleaner impregnated towels of the present invention results in a corresponding reduction in the transportation costs for the final product.

The non-aqueous formulation according to the present invention reduces the likelihood of the growth of opportunistic microorganisms on the impregnated cleaner compound, because of the absence of water. The cleaner impregnated towel according to the present invention includes an antimicrobial compound, and therefore is particularly desirable for use in hospitals, day care centers, nursing homes, and similar institutions. Finally, the inventive cleaner is mild and capable of generating a large amount of stable foam.

The inventive cleaner formulation according to the present invention comprises d-limonene. D-limonene is a terpene which occurs naturally in all plants. It is a monocyclic unsaturated terpene which is generally a by-product of the citrus industry, derived from the distilled rind oils of oranges, grapefruits, lemons, and the like. A discussion concerning d-limonene and its derivation from numerous sources is set forth in Kesterson, J. W., "Florida Citrus Oil," Institute of Food and Agriculture Science, University of Florida, December, 1971. D-limonene is commercially available from Florida Chemical Company and from SMC Glidco Organics. D-limonene may be present in the inventive formulation at a concentration from about 0.5 to about 90 weight percent. Preferably, the concentration of d-limonene is about 8 weight percent of the aqueous formulation and about 31.8 weight percent of the non-aqueous formulation.

Dibasic acid ester may be present in the inventive formulation at a concentration from about 0.5 to about 90 weight percent of the aqueous formulation. The term dibasic acid ester includes dialkyl esters of dicarboxylic aliphatic acids, and mixtures thereof. Suitable dibasic acid esters according to the present invention include, but are not necessarily limited to, dimethyl adipate, dimethyl succinate, dimethyl glutarate, and the like, as well as mixtures thereof. A preferred dibasic acid ester may be obtained from DuPont Chemicals of Wilmington, Del. under the trade name "DBE-1", which comprises a mixture of dimethyl glutarate, dimethyl adipate, and dimethyl succinate. Preferably, the concentration of dibasic acid ester is about 4 weight percent of the aqueous formulation and about 16 weight percent of the non-aqueous formulation.

N-methyl-2-pyrrolidone is a well-known compound used in the present formulation which acts as a dispersant. The concentration of N-methyl-2-pyrrolidone in the inventive cleaner may range from about 0.5 to about 45 weight percent of the aqueous formulation. Preferably, the concentration is about 5 weight percent of the aqueous formulation and about 20 weight percent of the non-aqueous formulation.

Secondary alcohol ethoxylate is present in the inventive formulation as a primary nonionic surfactant emulsifier and detergent. Useful secondary alcohol ethoxylates include C-12 to C-15 secondary alcohols having 5 moles average ethoxy moieties. A particularly useful secondary alcohol ethoxylate is available from Union Carbide Chemical Company under the trade designation "TERGITOL 15-S-5." The secondary alcohol ethoxylate may be present at a concentration from about 0.1 to about 50 weight percent of the aqueous formulation. Preferably, the secondary alcohol ethoxylate is present at a concentration of about 2.5 weight percent of the aqueous formulation and about 10 weight percent of the non-aqueous formulation.

Sodium lauryl sulfate acts as a wetting agent and thickener in the present formulation. The sodium lauryl sulfate may be present at a concentration from about 0.1 to about 50 weight percent of the aqueous formulation. Preferably, the concentration is about 1.5 weight percent of the aqueous formulation and about 6 weight percent of the non-aqueous formulation.

Polysorbate 80 (or polyoxyethylene (20) sorbitan monooleate) is present in the inventive formulation as a stabilizer. A preferred polysorbate 80 may be obtained from Van Water & Rogers Inc. carrying the product designation "TWEEN 80." The concentration of the polysorbate 80 may range from about 0.1 to about 50 weight percent of the aqueous formulation. Preferably, the concentration is about 2 weight percent of the aqueous formulation and about 8 weight percent of the non-aqueous formulation.

Glycerine is a well-known compound which is included in the inventive cleaner formulation as a skin conditioner and humectant. The glycerine may be present at a concentration from the about 0.1 to 25 weight percent of the aqueous formulation. Preferably, the glycerine is present at a concentration of about 0.5 weight percent of the aqueous formulation and about 2 weight percent of the non-aqueous formulation.

Ethyl alcohol is present in the inventive cleaner formulation to aid in the "dry off" of the formulation from the skin, and to provide a degree of product preservation due to its antimicrobial activity which is important in food service activities. The ethyl alcohol may be present at a concentration from about 0.1 to about 25 weight percent of the aqueous formulation. Preferably, the concentration is about 1.5 weight percent of the aqueous formulation and about 6 weight percent of the non-aqueous formulation.

The inventive cleaner formulation includes an antimicrobial preservative, to prevent microbial degradation. Examples of various antimicrobial agents, as well as their characteristics and method of preparation, are set forth in Kirk-Othmer, "Concise Encyclopedia of Chemical Technology," John Wiley & Sons, New York (1985) at pp. 104–106. Preferred antimicrobial preservatives include a blend of isothiazolinones available from Rohm and Haas Company of Philadelphia, Pa. under the product designation "KATHON CG/ICP." The antimicrobial preservative may be present at a concentration from about 0.01 to about 1 weight percent of the aqueous formulation. Preferably, the concentration is about 0.05 weight percent of the aqueous formulation and about 0.2 weight percent of the non-aqueous formulation.

Finally, water optionally may comprise one of the components of the inventive cleaner formulation; or, as explained earlier, the cleaner impregnated towels containing the non-aqueous cleaner formulation may be shipped to the ultimate user who then adds water to constitute the aqueous version of the product. The water may be present at a concentration from zero percent for the non-aqueous version of the cleaner formulation to 95 weight percent for the aqueous version. Preferably, the water concentration is about 75 weight percent for the aqueous version of the cleaner formulation.

The cleaner impregnated towels according to the present invention are particularly suited for use in the food processing industry, hospitals, and similar institutional settings where the expense, inconvenience, and harshness of products currently on the market preclude their frequent use for hand washing, which is desirable in order to preclude the spread of infectious microorganisms.

In operation a web of the flexible, porous substrate may be sprayed with the cleaner formulation, or alternatively, the substrate web may be conveyed through a wetting vat of the cleaner formulation. Thus, the substrate web is coated and infused with the cleaner.

The resultant cleaner impregnated substrate web may then be cut into desired sizes to produce individual cleaner impregnated towels. Each such towel includes a quantity of the cleaner adhered to the fibers or filaments within the porous structure of the product.

EXAMPLE I

A solution comprising the ingredients listed in Table I, in the approximate weight percentages indicated, is sprayed onto a web of non-woven material. The web, containing the impregnated solution, is cut to desired sized sheets and packaged in a sealed container, to prepare cleaner impregnated towels according to the present invention.

TABLE I

| AQUEOUS CLEANER FORMULATION | |
|---|---|
| Ingredient | Weight Percentage |
| d-limonene | 8 |
| dibasic acid ester (1) | 4 |
| N-methyl-2-pyrrolidone | 5 |
| secondary alcohol ethoxylate (2) | 2.5 |
| sodium lauryl sulfate | 1.5 |
| polysorbate 80 | 2 |
| glycerine | 0.5 |
| ethyl alcohol | 1.5 |
| antimicrobial preservative (3) | 0.05 |
| water | 74.95 |

(1) DBE-1, from Dupont Chemicals
(2) TERGITOL 15-S-5, from Union Carbide
(3) KATHON CG/ICP

EXAMPLE II

A non-aqueous solution comprising the ingredients listed in Table II, in the approximate weight percentages indicated, is sprayed onto a web of non-woven material. The web is perforated to define desired sized sheets, wound to form a roll, and placed into a sealed cylindrical container. The resultant cleaner impregnated towels according to the non-aqueous version of the present invention, may be constituted by the user by the addition of water to the container.

TABLE II

NON-AQUEOUS CLEANER FORMULATION

| Ingredient | Weight Percentage |
|---|---|
| d-limonene | 31.8 |
| dibasic acid ester (1) | 16 |
| N-methyl-2-pyrrolidone | 20 |
| secondary alcohol ethoxylate (2) | 10 |
| sodium lauryl sulfate | 6 |
| polysorbate 80 | 8 |
| glycerine | 2 |
| ethyl alcohol | 6 |
| antimicrobial preservative (3) | 0.2 |

(1) DBE-1, from DuPont Chemicals
(2) TERGITOL 15-S-5, from Union Carbide
(3) KATHON CG/ICP The cleaner impregnated towels described hereinabove generally have been described in terms of their broadest application to the practice of the present invention. Occasionally, however, the materials or the process conditions described may not be precisely applicable to each cleaner impregnated towel variant included within the disclosed scope. Those instances where this occurs will be readily recognized by those ordinarily skilled in the art. In all such cases, the product may be prepared and the process may successfully be performed by routine modifications to the disclosed product or process, e.g., other flexible, porous substrates may be used, or other methods of impregnating the substrate may be employed, etc., or modifications which are otherwise conventional may be made.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A cleaner impregnated towel, comprising:
a flexible, porous substrate; and
a cleaner impregnated into said substrate, said cleaner comprising:
from about 0.5 to about 90 weight percent d-limonene;
from about 0.5 to about 90 weight percent dibasic acid ester;
from about 0.5 to about 45 weight percent N-methyl-2-pyrrolidone;
from about 0.1 to about 50 weight percent secondary alcohol ethoxylate;
from about 0.1 to about 50 weight percent sodium lauryl sulfate;
from about 0.1 to about 50 weight percent polysorbate 80;
from about 0.1 to about 25 weight percent glycerine;
from about 0.1 to about 25 weight percent ethyl alcohol;
from about 0.01 to about 1 weight percent antimicrobial preservative; and optionally
from 0 to about 95 weight percent water.

2. The cleaner impregnated towel according to claim 1, wherein the substrate is non-woven.

3. The cleaner impregnated towel according to claim 1, wherein the substrate comprises fibers selected from the group consisting of wood, silk, jute, hemp, cotton, linen, polyolefins, polyesters, rayon, cellulose esters, polyvinyl derivatives, polyamides, and combinations thereof.

4. The cleaner impregnated towel according to claim 3, wherein the substrate fibers have a Denier from about 1.5 to about 5.

5. The cleaner impregnated towel according to claim 3, wherein the substrate fibers have lengths from about 5 mm to about 50 mm.

6. The cleaner impregnated towel according to claim 1, wherein the concentration of d-limonene is about 8 weight percent of the cleaner.

7. The cleaner impregnated towel according to claim 1, wherein the concentration of dibasic acid ester is about 4 weight percent of the cleaner.

8. The cleaner impregnated towel according to claim 1, wherein the concentration of N-methyl-2-pyrrolidone is about 5 weight percent of the cleaner.

9. The cleaner impregnated towel according to claim 1, wherein the concentration of secondary alcohol ethoxylate is about 2.5 weight percent of the cleaner.

10. The cleaner impregnated towel according to claim 1, wherein the concentration of sodium lauryl sulfate is about 1.5 weight percent of the cleaner.

11. The cleaner impregnated towel according to claim 1, wherein the concentration of polysorbate 80 is about 2 weight percent of the cleaner.

12. The cleaner impregnated towel according to claim 1, wherein the concentration of glycerine is about 0.5 weight percent of the cleaner.

13. The cleaner impregnated towel according to claim 1, wherein the concentration of ethyl alcohol is about 1.5 weight percent of the cleaner.

14. The cleaner impregnated towel according to claim 1, wherein the concentration of antimicrobial preservative is about 0.05 weight percent of the cleaner.

15. The cleaner impregnated towel according to claim 1, wherein the concentration of water is about 74.95 weight percent of the cleaner.

16. A cleaner impregnated towel, comprising a flexible, porous substrate, and a cleaner impregnated into said substrate, said cleaner comprising:
d-limonene at about 8 weight percent of the cleaner;
dibasic acid ester at about 4 weight percent of the cleaner;
N-methyl-2-pyrrolidone at about 5 weight percent of the cleaner;
secondary alcohol ethoxylate at about 2.5 weight percent of the cleaner;
sodium lauryl sulfate at about 1.5 weight percent of the cleaner;
polysorbate 80 at about 2 weight percent of the cleaner;
glycerine at about 0.5 weight percent of the cleaner;
ethyl alcohol at about 1.5 weight percent of the cleaner;
antimicrobial preservative at about 0.05 weight percent of the cleaner; and
water at about 74.95 weight percent of the cleaner.

17. The cleaner impregnated towel according to claim 1, wherein the concentration of d-limonene is about 31.8 weight percent of the cleaner.

18. The cleaner impregnated towel according to claim 1, wherein the concentration of dibasic acid ester is about 16 weight percent of the cleaner.

19. The cleaner impregnated towel according to claim 1, wherein the concentration of N-methyl-2-pyrrolidone is about 20 weight percent of the cleaner.

20. The cleaner impregnated towel according to claim 1, wherein the concentration of secondary alcohol ethoxylate is about 10 weight percent of the cleaner.

21. The cleaner impregnated towel according to claim 1, wherein the concentration of sodium lauryl sulfate is about 6 weight percent of the cleaner.

22. The cleaner impregnated towel according to claim 1, wherein the concentration of polysorbate 80 is about 8 weight percent of the cleaner.

23. The cleaner impregnated towel according to claim 1, wherein the concentration of glycerine is about 2 weight percent of the cleaner.

24. The cleaner impregnated towel according to claim 1, wherein the concentration of ethyl alcohol is about 6 weight percent of the cleaner.

25. The cleaner impregnated towel according to claim 1, wherein the concentration of antimicrobial preservation is about 0.2 weight percent of the cleaner.

26. A cleaner impregnated towel, comprising a flexible, porous substrate, and a cleaner impregnated into said substrate, said cleaner comprising:

d-limonene at about 31.8 weight percent of the cleaner;

dibasic acid ester at about 16 weight percent of the cleaner;

N-methyl-2-pyrrolidone at about 20 weight percent of the cleaner;

secondary alcohol ethoxylate at about 10 weight percent of the cleaner;

sodium lauryl sulfate at about 6 weight percent of the cleaner;

polysorbate 80 at about 8 weight percent of the cleaner;

glycerine at about 2 weight percent of the cleaner;

ethyl alcohol at about 6 weight percent of the cleaner; and antimicrobial preservative at about 0.2 weight percent of the cleaner.

* * * * *